United States Patent
Boguslavskiy et al.

(10) Patent No.: US 8,958,061 B2
(45) Date of Patent: Feb. 17, 2015

(54) HEATED WAFER CARRIER PROFILING

(75) Inventors: Vadim Boguslavskiy, Princeton, NJ (US); Joshua Mangum, Sarasota, FL (US); Matthew King, Montville, NJ (US); Earl Marcelo, South Plainfield, NJ (US); Eric A. Armour, Pennington, NJ (US); Alexander I. Gurary, Bridgewater, NJ (US); William E. Quinn, Whitehouse Station, NJ (US); Guray Tas, Flanders, NJ (US)

(73) Assignee: Veeco Instruments Inc., Plainview, NY (US)

( * ) Notice: Subject to any disclaimer, the term of this patent is extended or adjusted under 35 U.S.C. 154(b) by 408 days.

(21) Appl. No.: 13/483,491

(22) Filed: May 30, 2012

(65) Prior Publication Data
US 2012/0307233 A1    Dec. 6, 2012

Related U.S. Application Data

(60) Provisional application No. 61/491,486, filed on May 31, 2011.

(51) Int. Cl.
*G01N 21/00* (2006.01)
*H01L 21/687* (2006.01)
(Continued)

(52) U.S. Cl.
CPC .... *H01L 21/68764* (2013.01); *H01L 21/67109* (2013.01); *H01L 21/68771* (2013.01); *C23C 16/4584* (2013.01); *C23C 16/46* (2013.01); *C23C 16/52* (2013.01)
USPC ............... 356/237.2; 356/43; 356/51; 438/16

(58) Field of Classification Search
USPC ........ 356/15, 231.1–241.6, 43, 45, 51; 374/1, 374/2; 438/14, 16
See application file for complete search history.

(56) References Cited

U.S. PATENT DOCUMENTS

| 4,592,306 A | 6/1986 | Gallego |
| 4,687,344 A | 8/1987 | Lillquist |

(Continued)

FOREIGN PATENT DOCUMENTS

| JP | 49-80975 | 8/1974 |
| JP | 62-144318 A | 6/1987 |

(Continued)

OTHER PUBLICATIONS

Japanese Office Action for Application No. 2012-175252 dated Nov. 22, 2013.

(Continued)

*Primary Examiner* — Tarifur Chowdhury
*Assistant Examiner* — Michael P Lapage
(74) *Attorney, Agent, or Firm* — Lerner, David, Littenberg, Krumholz & Mentlik, LLP

(57) ABSTRACT

A method for characterizing a surface comprises rotating a carrier about an axis of rotation where the carrier has a top surface adapted to hold at least one semiconductor wafer with a major surface of the wafer extending generally transverse to the axis of rotation. A surface characterization tool is moved over a plurality of positions relative to the top surface of the carrier, where a measurement location over the top surface of the carrier is changed while said top surface of the carrier is heated to a predetermined temperature. Characterization signals over the plurality of positions with the surface characterization tool are produced and contain information about the heated top surface of the carrier, or when semiconductor wafers are held on the carrier, information about the semiconductor wafer can also be obtained.

33 Claims, 5 Drawing Sheets

(51) Int. Cl.
*H01L 21/67* (2006.01)
*C23C 16/458* (2006.01)
*C23C 16/46* (2006.01)
*C23C 16/52* (2006.01)

(56) References Cited

U.S. PATENT DOCUMENTS

| | | | |
|---|---|---|---|
| 4,763,602 | A | 8/1988 | Madan et al. |
| 4,770,121 | A | 9/1988 | Ebata et al. |
| 5,213,985 | A | 5/1993 | Sandroff et al. |
| 5,282,921 | A | 2/1994 | Poultney |
| 5,333,413 | A | 8/1994 | Hashimoto |
| 5,871,805 | A | 2/1999 | Lemelson |
| 6,099,596 | A | 8/2000 | Li et al. |
| 6,135,854 | A | 10/2000 | Masumura et al. |
| 6,184,498 | B1 * | 2/2001 | Kiyama .................... 219/390 |
| 6,349,270 | B1 | 2/2002 | Gurary et al. |
| 6,492,625 | B1 * | 12/2002 | Boguslavskiy et al. ....... 219/486 |
| 7,130,762 | B2 | 10/2006 | Hellig et al. |
| 7,159,599 | B2 | 1/2007 | Verhaverbeke et al. |
| 7,276,124 | B2 | 10/2007 | Gurary et al. |
| 7,368,368 | B2 | 5/2008 | Emerson |
| 8,021,487 | B2 | 9/2011 | Boguslavskiy et al. |
| 8,022,372 | B2 | 9/2011 | Lee et al. |
| 8,198,605 | B2 | 6/2012 | Lee et al. |
| 2001/0013313 | A1 | 8/2001 | Droopad et al. |
| 2002/0068371 | A1 | 6/2002 | Yun |
| 2004/0060917 | A1 | 4/2004 | Liu et al. |
| 2004/0083955 | A1 | 5/2004 | Ramsay |
| 2004/0246493 | A1 | 12/2004 | Kim et al. |
| 2005/0286058 | A1 | 12/2005 | Belousov et al. |
| 2006/0171442 | A1 * | 8/2006 | Volf et al. .................... 374/1 |
| 2007/0140826 | A1 | 6/2007 | Ho et al. |
| 2007/0291816 | A1 | 12/2007 | Volf et al. |
| 2008/0126014 | A1 | 5/2008 | Cui et al. |
| 2009/0027657 | A1 | 1/2009 | Serebryanov et al. |
| 2009/0224175 | A1 * | 9/2009 | Lee et al. .................... 250/459.1 |
| 2009/0296081 | A1 | 12/2009 | Plug et al. |
| 2010/0055318 | A1 * | 3/2010 | Volf et al. ................ 427/255.28 |
| 2010/0124249 | A1 * | 5/2010 | Aderhold et al. ............. 374/124 |
| 2010/0292950 | A1 | 11/2010 | Iuchi et al. |
| 2011/0308453 | A1 | 12/2011 | Su et al. |
| 2012/0170609 | A1 * | 7/2012 | Gurary et al. ..................... 374/2 |
| 2012/0248336 | A1 | 10/2012 | Lee et al. |

FOREIGN PATENT DOCUMENTS

| | | |
|---|---|---|
| JP | 62-189724 A | 8/1987 |
| JP | 2007-005645 A | 1/2007 |
| JP | 2007-318031 A | 12/2007 |
| JP | 2011-514660 A | 5/2011 |
| KR | 2003-0094491 A | 12/2003 |
| KR | 2007-0054453 A | 5/2007 |
| WO | 2008/005773 A2 | 1/2008 |
| WO | 2009/099776 A1 | 8/2009 |

OTHER PUBLICATIONS

International Search Report, PCT/US2009/001006, dated Aug. 13, 2009.
International Search Report, PCT/US2009/031831, dated Jun. 29, 2009.
Y. Nakano et al., "Strong Photoluminescenceand Low Surface State Densities on Clean and Silicon Deposited (001) Surfaces of GaAs with (4×6) Reconstruction." Jpn. J. Appl. Phys. 41 (Apr. 2002) pp. 2542-2547. <doi: 10.1143/JJAP.41.2542>.
C. J. Wang et al., "In-line FTIR for expitaxial silicon film thickness measurement on an Applied Materials Centura cluster tool." Advanced Semiconductor Manufactering Conference and Workshop, 1994, ASMC 94 Proceedings, IEEE/SEMI. (Nov. 1994) pp. 229-231. <doi: 10.1109/ASMC.1994.588256>.
International Search Report and Written Opinion for Application No. PCT/US2012/039947 dated Dec. 26, 2012.

* cited by examiner

HEATED WAFER CARRIER PROFILING

CROSS-REFERENCE TO RELATED APPLICATIONS

The present application claims the benefit of the filing date of U.S. Provisional Patent Application Ser. No. 61/491,486, filed May 31, 2011, the disclosure and contents of which are hereby incorporated by reference herein.

FIELD OF THE INVENTION

The present invention relates to chemical vapor deposition methods and apparatus.

BACKGROUND OF THE INVENTION

Chemical vapor deposition is a process in which layers of one or more materials are deposited on a substrate by reaction of materials supplied as gasses or vapors. For example, devices formed from compound semiconductors such as III-V semiconductors typically are formed by growing successive layers of the compound semiconductor using a form of chemical vapor deposition referred to as metal organic chemical vapor deposition or "MOCVD." In this process, the wafers are exposed to a combination of gases, typically including a metal organic compound as a source of a Group III metal, and also including a source of a Group V element which flow over the surface of the wafer while the wafer is maintained at an elevated temperature. Typically, the metal organic compound and Group V source are combined with a carrier gas which does not participate appreciably in the reaction as, for example, nitrogen. One example of a III-V semiconductor is gallium nitride, which can be formed by reaction of an organo gallium compound and ammonia on a substrate having a suitable crystal lattice spacing, as for example, a sapphire wafer. Typically, the wafer is maintained at a temperature on the order of from about 400 to about 1300° C. during deposition of gallium nitride and related compounds.

Composite devices can be fabricated by depositing numerous layers in succession on the surface of the wafer under slightly different reaction conditions as, for example, additions of other Group III or Group V elements to vary the crystal structure and bandgap of the semiconductor. For example, in a gallium nitride based semiconductor, indium, aluminum or both can be used in varying proportion to vary the bandgap of the semiconductor. Also, p-type or n-type dopants can be added to control the conductivity of each layer. After all of the semiconductor layers have been formed and, typically, after appropriate electric contacts have been applied, the wafer is cut into individual devices. Devices such as light-emitting diodes ("LEDs"), lasers, and other optoelectronic devices can be fabricated in this way.

In a typical chemical vapor deposition process, numerous wafers are held on a device commonly referred to as a wafer carrier so that a top surface of each wafer is exposed at a surface of the wafer carrier referred to herein as the top or first surface. The wafer carrier is then placed into a reaction chamber and maintained at the desired temperature while the gas mixture flows over the surface of the wafer carrier. It is important to maintain uniform conditions at all points on the top surfaces of the various wafers on the carrier during the process. Minor variations in composition of the reactive gases and in the temperature of the wafer surfaces cause undesired variations in the properties of the resulting semiconductor device. For example, if a gallium and indium nitride layer is deposited, variations in wafer surface temperature will cause variations in the composition and bandgap of the deposited layer. If the deposited layer is an active, light-emitting layer of an LED structure, the emission wavelength of the LEDs formed from the wafers will also vary. Thus, considerable effort has been devoted in the art heretofore towards maintaining uniform conditions.

One type of CVD apparatus which has been widely accepted in the industry uses a wafer carrier in the form of a large disc with numerous wafer-holding regions, each adapted to hold one wafer. The wafer carrier is supported on a spindle within the reaction chamber so that the top or first surface of the wafer carrier having the exposed surfaces of the wafers faces upwardly toward a gas distribution element. While the spindle is rotated, the gas is directed downwardly onto the top surface of the wafer carrier and flows across the top surface toward the periphery of the wafer carrier. The used gas is evacuated from the reaction chamber through ports disposed below the wafer carrier. The wafer carrier is maintained at the desired elevated temperature by heating elements, typically electrical resistive heating elements disposed below the wafer carrier. These heating elements are maintained at a temperature above the desired temperature of the wafer surfaces, whereas the gas distribution element typically is maintained at a temperature well below the desired reaction temperature so as to prevent premature reaction of the gases. Therefore, heat is transferred from the heating elements to the bottom or second surface of the wafer carrier (the surface facing in the opposite direction from the top surface) and flows upwardly through the wafer carrier to the individual wafers.

SUMMARY OF THE INVENTION

The present invention provides an apparatus for performing non-contact surface characterization. The apparatus provides a carrier rotatable about an axis of rotation where the carrier has a top surface adapted to hold at least one semiconductor wafer and a surface characterization tool which is operative to move over a plurality of positions relative to the top surface of the carrier and/or the wafer transverse to the axis of rotation. The surface characterization tool is operative to move over a plurality of positions relative to the top surface of the carrier and/or the wafer transverse to the axis of rotation and is further adapted to produce characterization signals over the plurality of positions on at least a portion of said carrier and/or on at least a portion of said major surface of said wafer as said carrier rotates. The apparatus can further provide a chemical vapor deposition chamber and a computer that is coupled to the surface characterization tool.

The present invention also provides a system for optimizing chemical vapor deposition. The system comprises a surface characterization tool adapted to measure a surface characteristic over a plurality of positions relative to a rotatable carrier having a top surface adapted to hold at least one semiconductor wafer, where the surface characterization tool is adapted to produce characterization signals, which contain information about the top surface of the carrier and/or wafer, over the plurality of positions, and a first computer having a memory for storing a set of computer instructions, where the computer is in communication with the surface characterization tool for determining values for position-dependent parameters characterizing the top surface of the carrier based on the characterization signals obtained during each process step of a chemical vapor deposition run. In addition there is a chemical vapor deposition chamber in which a carrier rotatable about an axis of rotation and having a top surface adapted to hold at least one semiconductor wafer with a major surface of the wafer extending generally transverse to the axis of rotation is placed. In the chamber is a heater which is proximately placed to the carrier. The heater has one or more heating elements. Additionally, one or more gas sources, to supply gases including a Group III metal source and a Group V compound into the chamber, are also provided. A second computer is also provided and is communication with the heater, the one or more gas sources, and/or the first computer. The first computer can communicate the position-dependent parameters from the surface characterization tool during each step of a chemical vapor deposition run to the second computer, which can then adjust the heaters and/or gas sources in the chamber to increase yield in the chamber.

The present invention also provides a method for characterizing a surface. The method comprises rotating a carrier about an axis of rotation where the carrier has a top surface adapted to hold at least one semiconductor wafer with a major surface of the wafer extending generally transverse to the axis of rotation. A surface characterization tool is moved over a plurality of positions relative to the top surface of the carrier, where a measurement location over the top surface of the carrier is changed while said top surface of the carrier is heated to a predetermined temperature. Characterization signals over the plurality of positions with the surface characterization tool are produced and the characterization signals contain information about the heated top surface of the carrier, or when one or more semiconductor wafers are held on the carrier, not only is information about the heated top surface of the carrier acquired, but also information about the semiconductor wafer, for example, the temperature of the wafer surface, any bowing, tilting or warping of the semiconductor wafer can also be obtained. Additionally, photoluminescence, electroluminescence, reflectance, and emissivity can also be measured. Values of position-dependent parameters characterizing the top surface of the carrier based on the characterization signals are then determined. Examples of such parameters or surface properties include temperature, reflectance, photoluminescence, electroluminescence, emissivity, and absence or presence of residual deposits from a chemical vapor deposition.

The present invention also provides another method for characterizing a surface. The method comprises rotating a carrier about an axis of rotation where the carrier has a top surface adapted to hold at least one semiconductor wafer with a major surface of the wafer extending generally transverse to the axis of rotation. A surface characterization tool is moved over a plurality of positions relative to the top surface of the carrier, where a measurement location over the top surface of the carrier is changed. Characterization signals over the plurality of positions with the surface characterization tool are produced and the characterization signals contain information about the top surface of the carrier. Values of position-dependent parameters characterizing the top surface of the carrier based on the characterization signals are then determined. Examples of such parameters or surface properties include temperature, reflectance, photoluminescence, electroluminescence, emissivity, and absence or presence of residual deposits from a chemical vapor deposition.

The surface characterization tool can be one or more metrology tools that are typically used in MOCVD processes. Such tools include a pyrometer, reflectometer, a combined pyrometer/reflectometer, a combined deflectometer/reflectometer/temperature tool, ellipsometer, photoluminescence spectrometer, camera, electroluminescence spectrometer, surface acoustic wave generator, or any combination thereof. The camera can be a digital camera or traditional camera that uses developable film. In addition, the camera can record images using visible light, ultraviolet or infrared light.

Instructions are stored on the computers and include instructions for correlating the characterization signals to its positions on the top surface of the carrier, comparing characterization signals of the top surface of the carrier to a reference carrier top surface on a position by position basis, displaying the characterization signals to its positions on the top surface of the carrier in a visually perceptible manner, storing the position-dependent characterization signals during each process step of a chemical vapor deposition run; instructions for obtaining position-dependent characterization signals from a calibration wafer, comparing the position-dependent characterization signals from each process step of the chemical vapor deposition run to a predetermined set of optimal position-dependent characterization signals comparing the position-dependent characterization signals from each process step of the chemical vapor deposition run to a set of position-dependent characterization signals from a calibration wafer, and adjusting the process steps of a chemical vapor deposition run based on the comparison of the position-dependent characterization signals from each process step of the chemical vapor deposition run to the set of position-dependent characterization signals from a calibration wafer. Other instructions include providing a feedback loop between the surface characterization tool and the heater so that the temperature of the wafer carrier and/or the wafers located thereon, is regulated.

In other instances, a plurality of carriers can be evaluated using the apparatus and/or methods described above. When a plurality of carriers are sequentially characterized in the chamber, the set of computer instructions include those for correlating the characterization signals on a position by position basis of the top surface of each carrier separately characterized in the chamber, storing the characterization signals on a position by position basis from the top surface of each carrier sequentially characterized in the chamber in a database, performing a analysis on the characterization signals of the plurality of carriers on a position by position basis, and displaying a surface characteristic map from the characterization signals on a position by position basis from the top surface of each carrier sequentially characterized in the chamber.

DETAILED DESCRIPTION

Figures 1, 2:
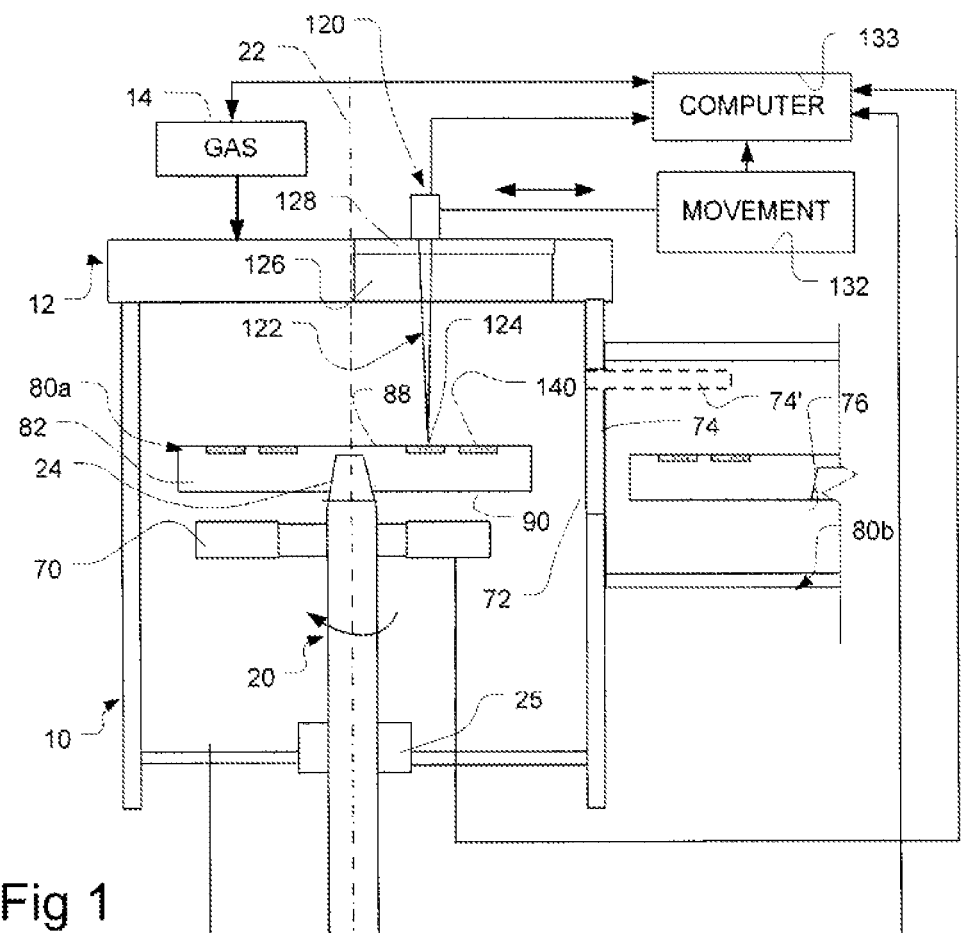
FIG. 1 is a simplified, schematic sectional view depicting chemical vapor deposition apparatus in accordance with one embodiment of the invention.
FIG. 2 is a diagrammatic top plan view of the apparatus of FIG. 1.

The present invention provides an apparatus for performing non-contact surface characterization. The apparatus provides a carrier rotatable about an axis of rotation where the carrier has a top surface adapted to hold at least one semiconductor wafer and a surface characterization tool which is operative to move over a plurality of positions relative to the top surface of the carrier and/or the wafer transverse to the axis of rotation. The surface characterization tool is operative to move over a plurality of positions relative to the top surface of the carrier and/or the wafer transverse to the axis of rotation and is further adapted to produce characterization signals over the plurality of positions on at least a portion of said carrier and/or on at least a portion of said major surface of said wafer as said carrier rotates. The apparatus can further provide a chemical vapor deposition chamber and a computer that is coupled to the surface characterization tool.

The present invention also provides a system for optimizing chemical vapor deposition. The system comprises a surface characterization tool adapted to measure a surface characteristic over a plurality of positions relative to a rotatable carrier having a top surface adapted to hold at least one semiconductor wafer, where the surface characterization tool is adapted to produce characterization signals, which contain information about the top surface of the carrier and/or wafer, over the plurality of positions, and a first computer having a memory for storing a set of computer instructions, where the computer is in communication with the surface characterization tool for determining values for position-dependent parameters characterizing the top surface of the carrier based on the characterization signals obtained during each process step of a chemical vapor deposition run. In addition there is a chemical vapor deposition chamber in which a carrier rotatable about an axis of rotation and having a top surface adapted to hold at least one semiconductor wafer with a major surface of the wafer extending generally transverse to the axis of rotation is placed. In the chamber is a heater which is proximately placed to the carrier. The heater has one or more heating elements. Additionally, one or more gas sources, to supply gases including a Group III metal source and a Group V compound into the chamber, are also provided. A second computer is also provided and is communication with the heater, the one or more gas sources, and/or the first computer. The first computer can communicate the position-dependent parameters from the surface characterization tool during each step of a chemical vapor deposition run to the second computer, which can then adjust the heaters and/or gas sources in the chamber to increase yield in the chamber.

The present invention also provides a method for characterizing a surface. The method comprises rotating a carrier about an axis of rotation where the carrier has a top surface adapted to hold at least one semiconductor wafer with a major surface of the wafer extending generally transverse to the axis of rotation. A surface characterization tool is moved over a plurality of positions relative to the top surface of the carrier, where a measurement location over the top surface of the carrier is changed while said top surface of the carrier is heated to a predetermined temperature. Characterization signals over the plurality of positions with the surface characterization tool are produced and the characterization signals contain information about the heated top surface of the carrier, or when one or more semiconductor wafers are held on the carrier, not only is information about the heated top surface of the carrier acquired, but also information about the semiconductor wafer, for example, the temperature of the wafer surface, any bowing, tilting or warping of the semiconductor wafer can also be obtained. Values of position-dependent parameters characterizing the top surface of the carrier based on the characterization signals are then determined.

The present invention also provides another method for characterizing a surface. The method comprises rotating a carrier about an axis of rotation where the carrier has a top surface adapted to hold at least one semiconductor wafer with a major surface of the wafer extending generally transverse to the axis of rotation. A surface characterization tool is moved over a plurality of positions relative to the top surface of the carrier, where a measurement location over the top surface of the carrier is changed. Characterization signals over the plurality of positions with the surface characterization tool are produced and the characterization signals contain information about the top surface of the carrier. Values of position-dependent parameters characterizing the top surface of the carrier based on the characterization signals are then determined.

The surface characterization tool can be one or more metrology tools that are typically used in MOCVD processes. Such tools include a pyrometer, reflectometer, a combined pyrometer/reflectometer, a combined deflectometer/reflectometer/temperature tool, ellipsometer, photoluminescence spectrometer, camera, electroluminescence spectrometer, surface acoustic wave generator, or any combination thereof. The camera can be a digital camera or traditional camera that uses developable film. In addition, the camera can record images using visible light, ultraviolet or infrared light. The pyrometer can be an infrared pyrometer, which operates within the infrared spectrum, typically from about 900 nm to about 950 nm. The infrared pyrometer can often be used to measure the relative temperature of a wafer sitting in a wafer pocket since the infrared pyrometer cannot measure GaN and/or sapphire wafer temperature as they do not emit or absorb thermal radiance within the wavelength of the infrared pyrometer, even at temperatures ranging from 750° C. to 1100° C. The infrared pyrometer will give a general thermal profile of each wafer in each pocket, which can be compared against similarly situated wafers (for example, in each ring of the wafer carrier, depending upon the orientation of the pockets on the carrier) where the thermal profile is based on temperature between the pocket and the bottom of the wafer. Another type of pyrometer is one which operates at a wavelength of from about 400 to about 420 nm, commonly called a 'blue pyrometer'. Since the blue pyrometer operates at a different wavelength, by heating the wafers to 700° C. or hotter, the sapphire wafer becomes opaque and the actual temperature of the wafer surface can be realized. This is important since emissivity of the carrier can change due to diffuse reflectivity at high temperatures, in some instances as much as 10%, which can result in temperature differences of about 6° C. In general, pyrometers that operate at a wavelength of from about 400 nm to about 8 µm, more from about 400 nm to about 1000 nm, are suitable for use in the present invention.

Instructions are stored on the computers and include instructions for correlating the characterization signals to its positions on the top surface of the carrier, comparing characterization signals of the top surface of the carrier to a reference carrier top surface on a position by position basis, displaying the characterization signals to its positions on the top surface of the carrier in a visually perceptible manner, storing the position-dependent characterization signals during each process step of a chemical vapor deposition run; instructions for obtaining position-dependent characterization signals from a calibration wafer, comparing the position-dependent characterization signals from each process step of the chemical vapor deposition run to a predetermined set of optimal position-dependent characterization signals comparing the position-dependent characterization signals from each process step of the chemical vapor deposition run to a set of position-dependent characterization signals from a calibration wafer, and adjusting the process steps of a chemical vapor deposition run based on the comparison of the position-dependent characterization signals from each process step of the chemical vapor deposition run to the set of position-dependent characterization signals from a calibration wafer. Other instructions include providing a feedback loop between the surface characterization tool and the heater so that the temperature of the wafer carrier and/or the wafers located thereon, is regulated.

In other instance, a plurality of carriers can be evaluated using the apparatus and/or methods described above. When a plurality of carriers are sequentially characterized in the chamber, the set of computer instructions include those for correlating the characterization signals on a position by position basis of the top surface of each carrier separately characterized in the chamber, storing the characterization signals on a position by position basis from the top surface of each carrier sequentially characterized in the chamber in a database, performing a analysis on the characterization signals of the plurality of carriers on a position by position basis, and displaying a surface characteristic map from the characterization signals on a position by position basis from the top surface of each carrier sequentially characterized in the chamber.

In another instance, the present application also provides a method of controlling a chemical vapor deposition process utilizing a wafer carrier having a first surface, where the carrier is adapted to hold wafers exposed at the first surface, where one or more images of radiant energy emissions from the first surface of the carrier while maintaining the carrier at an elevated temperature are acquired, and then examining the one or more images. The first image can be acquired before the wafer carrier has been used in any deposition cycle as well as after a first cleaning cycle and before a subsequent deposition cycle.

Chemical vapor deposition apparatus in accordance with one embodiment of the invention includes a reaction chamber 10 having a gas distribution element 12 arranged at one end of the chamber. The end having the gas distribution element 12 is referred to herein as the "top" or "upstream" end of the chamber 10. This end of the chamber typically, but not necessarily, is disposed at the top of the chamber in the normal gravitational frame of reference. Thus, the downward direction as used herein refers to the direction away from the gas distribution element 12; whereas the upward direction refers to the direction within the chamber, toward the gas distribution element 12, regardless of whether these directions are aligned with the gravitational upward and downward directions. Similarly, the "top" and "bottom" surfaces of elements are described herein with reference to the frame of reference of chamber 10 and element 12.

Gas distribution element 12 is connected to one or more sources 14, which are in communication with computer 133, for supplying process gases to be used in the wafer treatment process, such as a carrier gas and reactant gases such as a metalorganic compound and a source of a Group V metal. The gas distribution element is arranged to receive the various gases and direct a flow of process gasses generally in the downward direction. The gas distribution element 12 may be connected to a coolant system (not shown) arranged to circulate a liquid through the gas distribution element so as to maintain the temperature of the element at a desired temperature during operation. A similar coolant arrangement (not shown) can be provided for cooling the walls of chamber 10. Chamber 10 is also equipped with an exhaust system 18 arranged to remove spent gases from the interior of the chamber through ports (not shown) at or near the bottom of the chamber so as to permit continuous flow of gas in the downward direction from the gas distribution element.

A spindle 20 is arranged within the chamber so that the central axis 22 of the spindle extends in the upward and downward directions. The spindle is mounted to the chamber by a conventional rotary pass-through device 25 incorporating bearings and seals (not shown) so that the spindle can rotate about axis 22, while maintaining a seal between the spindle and the wall of chamber 10. The spindle has a fitting 24 at its top end, i.e., at the end of the spindle closest to the gas distribution element 12. As further discussed below, fitting 24 is adapted to releasably engage a wafer carrier. In the particular embodiment depicted, the fitting 24 is a generally frustoconical element tapering toward the top end of the spindle and terminating at a flat top surface. A frustoconical element is an element having the shape of a frustum of a cone. Spindle 20 is connected to a rotary drive mechanism 26 such as an electric motor drive, which is arranged to rotate the spindle about axis 22.

A heating element 70 is mounted within the chamber and surrounds spindle 20 below fitting 24. The chamber is also provided with an entry opening 72 leading to an antechamber 76, and a door 74 for closing and opening the entry opening. Door 74 is depicted only schematically in FIG. 1 and is shown as movable between the closed position shown in solid lines, in which the door isolates the interior of chamber 10 from antechamber 76, and an open position shown in broken lines at 74'. The door 74 is equipped with an appropriate control and actuation mechanism for moving it between the open position and closed positions. In practice, the door may include a hoop-like shutter movable in the upward and downward directions as disclosed, for example, in U.S. Pat. No. 7,276,124, the disclosure of which is hereby incorporated by reference herein. The apparatus further includes a loading mechanism (not shown) capable of moving a wafer carrier from the antechamber 76 into the chamber and engaging the wafer carrier with the spindle in the operative condition, and also capable of moving a wafer carrier off of the spindle and into the antechamber.

Figure 3:
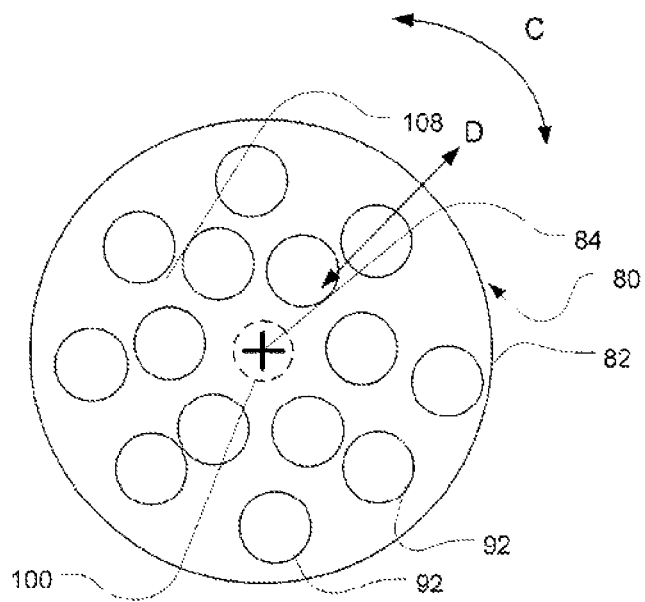
FIG. 3 is a diagrammatic top plan view of an element used in the apparatus of FIGS. 1 and 2.

The apparatus also includes a plurality of wafer carriers 80. In the operating condition shown in FIG. 1, a first wafer carrier 80a is disposed inside chamber 10 in an operative position, whereas a second wafer carrier 80b is disposed within antechamber 76. Each wafer carrier 80 includes a body 82 which is substantially in the form of a circular disc having a central axis 84 (FIG. 3). In the operative position shown in FIG. 1, the central axis 84 of the wafer carrier body is coincident with the axis 22 of the spindle. The body 82 may be formed as a single piece or as a composite of plural pieces. For example, as disclosed in U.S. Pat. No. 8,021,487, the disclosure of which is hereby incorporated by reference herein, the wafer carrier body may include a hub defining a small region of the body surrounding the central axis 84 and a larger portion defining the remainder of the disc-like body. The body desirably is formed from materials which do not contaminate the process and which can withstand the temperatures encountered in the process. For example, the larger portion of the disc may be formed largely or entirely from materials such as graphite, silicon carbide, or other refractory materials. The wafer carrier may include a coating covering the material of the body as, for example, a coating of silicon carbide overlying a body formed from graphite. The coating typically covers the top or first surface of the body, and may cover other surfaces of the body as well. The body has a generally planar top or first surface 88 and an oppositely-facing bottom surface 90 (FIGS. 1 and 4) extending generally parallel to one another and generally perpendicular to the central axis 84 of the disc.

The body also has a plurality of wafer-holding features adapted to hold a plurality of wafers.

Figure 4:
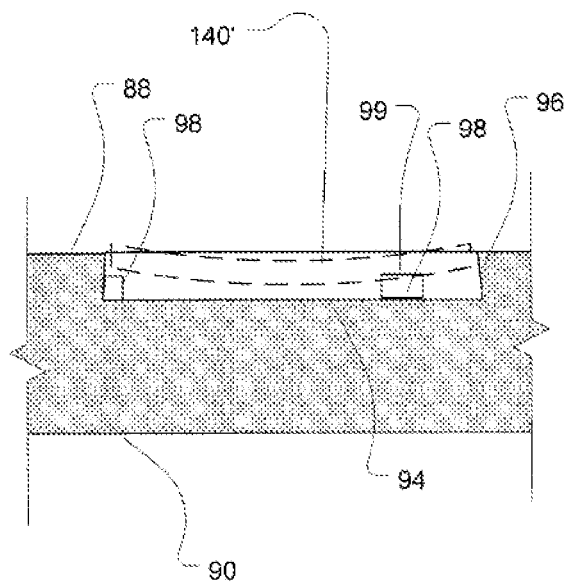
FIG. 4 is a fragmentary sectional view depicting a portion of the element of FIG. 3.

In the particular depicted embodiment of the carrier each wafer-holding feature includes a generally circular pocket 92 (FIGS. 3 and 4) extending downwardly into the body from the top or first surface 88. Each pocket has a floor surface 94 disposed below the surrounding portions of the top surface 88. Each pocket also has a peripheral wall surface 96 surrounding the floor surface and defining the periphery of the pocket. The peripheral wall surface 96 extends downwardly from the top surface 88 of the body to the floor surface. As best seen in FIG. 4, the peripheral wall surface may slope outwardly, away from the center of the pocket, over at least a portion of the periphery. In particular, those portions of the peripheral wall surface furthest from the central axis 84 of the wafer carrier desirably slope outwardly, away from the central axis 84 of the wafer carrier in the direction down toward the floor surface 94. Each pocket 90 is also provided with a plurality of spaced-apart supports 98 extending upwardly from the floor surface 94 and defining a wafer support surface 99 above the floor surface but below the first or top surface 88 of the wafer carrier body. In an alternative arrangement, the spaced-apart supports may be replaced by a unitary lip extending around the entire circumference of the pocket so as to define a continuous support surface. Other types of wafer-holding features can be used as well.

The wafer carrier also includes a fitting 100 at central axis 84. Fitting 100 is arranged to engage with the fitting 24 of the spindle. The fitting 100 includes a frustoconical recess 100 having a downwardly facing open end 102 (FIG. 2). The frustoconical recess is closed at its top end 104, and tapers in the upward direction. The frustoconical fitting 100 has an included angle slightly larger than the included angle of the male frustoconical fitting 24 of the spindle. In the operative condition shown, the frustoconical fitting 24 of the spindle is engaged within the fitting 100 of the wafer carrier and abuts the wafer carrier along a generally circular line of engagement. This arrangement provides a stable mounting for the wafer carrier, so that the wafer carrier is held firmly fixed in position, but can be disengaged by lifting the wafer carrier upwardly along axis 22.

Gas inlet element 12 has an elongated slot 126 (FIG. 1) extending generally radially, towards and away from axis 22. The slot is covered by a window 128 formed from a material transparent to infrared and visible radiation. The apparatus further includes a surface characterization tool 120 arranged to receive characterization signal 122 from a small region or point 124 referred to herein as the "viewpoint" of the tool, and to provide data representing such characterization signal. The tool may be selected from a pyrometer, reflectometer, a combined pyrometer/reflectometer, a combined deflectometer/reflectometer/temperaturetool, ellipsometer, photoluminescence spectrometer, camera, electroluminescence spectrometer, surface acoustic wave generator, or any combination thereof. Tool 120 is slidably mounted on a track 130 (FIG. 2) which in turn is mounted to the gas inlet element and thus mounted to chamber 10. The tool is linked to a movement device 132 such as a conventional mechanical, electromechanical, or pneumatic actuator so that tool 120 can be moved along slot 126, in alignment with window 128, in directions D towards and away from axis 22. As best appreciated with reference to FIG. 1, movement of tool 120 will also move the viewpoint 124 in directions D over the first or top surface of the wafer carrier disposed on the spindle. Movement device 132 may be arranged to provide a signal representing the radial position of the tool and viewpoint.

A surface acoustic wave generator can also be used to measure and evaluate thin film/surface combinations. Surface acoustic waves can measure the temperature and/or thickness of a thin film/substrate combination (for example, GaN/Si or GaN/sapphire). A first laser sends a signal to the surface of the thin film/substrate combination and a second probe laser detects the signal. By knowing the distance between signals where they hit the surface and measuring the time interval between surface wave generation and detection, velocity of the surface acoustic wave can be determined. As there is a temperature dependence related to the surface acoustic wave, the temperature of the thin film/substrate combination can be measured and monitored. At the same time, taking into account the surface acoustic wave frequency dependence on film thickness, the thickness of the thin film grown on the substrate can also be monitored. Using the temperature measurements with an active or feedback loop for heaters in MOCVD reactors, process temperatures can be monitored and controlled as described herein. Additionally, using the surface acoustic wave frequency dependence of thin film growth on substrates (for example, Si or sapphire), film thickness and integrity can also be monitored and measured.

Tool 120 may be arranged to provide data representing the characterization signal emanating from viewpoint 124 as one or more digital or analog signals. For example, if the tool is a pyrometer, it may be arranged to provide a "raw" signal representing the intensity of radiation emitted from the surface and thus representing the product of the emissivity of the carrier surface at the viewpoint multiplied by the fourth power of the absolute temperature of the carrier surface at the viewpoint. Such a raw signal thus includes information as to both emissivity and temperature. The tool optionally may also be arranged to provide a separate signal representing only the emissivity of the carrier surface at the viewpoint, so that temperature and emissivity can be deconvoluted. For example, the pyrometer tool may be arranged to direct a beam of radiant energy onto the surface at the viewpoint and detect the radiant energy reflected from the surface at the viewpoint. Another useful tool is a combined pyrometer/reflectometer as disclosed, for example, in U.S. Pat. No. 6,349,270, the contents of which are hereby incorporated herein by reference. Another useful too is a combined deflectometer, reflectometer, and temperature tool, available as a DRT-210 in-situ process monitor from Veeco Instruments.

Tool 120 is connected to computer 133. Computer 133 is also connected to movement device 132 for receipt of a signal representing the radial position of viewpoint 124. Computer 133 also receives a signal from rotary drive 26 representing the rotational position of spindle 20 and wafer carrier 80. As the spindle and carrier rotate, the viewpoint 124 of the tool sweeps over the first surface 88 of the carrier in circumferential directions C (FIG. 3) around the central axis 84 of the carrier. As the tool moves in directions D, viewpoint sweeps over the surface in the radial directions D. Computer 133 associates the data received from tool 120 at any instant with the radial position D and circumferential position C of the viewpoint at such instant. Such association may be explicit, as by recording the positions along with the data, or implicit, as by writing the data into an array in which the address of data in the array corresponds to the radial and circumferential positions. Thus, computer 133 creates a two-dimensional map of the first surface of the wafer carrier, plotting data representing characterization signal against location on the carrier surface. Such a two-dimensional map constitutes an image. The image can be displayed in visually-perceptible form, on, for example, a monitor.

Computer 133 can comprise a central processing unit (not shown), a memory (not shown), supporting circuitry (not shown), and an operator interface (which can include a keyboard, monitor, and other components that allow an operator to manually input information or upload stored information from other media (not shown)). Computer 133 allows for the control of the operating parameters and activities of chamber 10, as well as controlling process gas supply 14, heater 70, rotary drive 26, and tool 120. Computer 133 also allows for a feedback loop between tool 120 and heater 70 so that the temperature of wafer carrier 80 and, where appropriate, the temperature of wafers 140, can be regulated. The types and make-up of the central processing unit and memory are well known to those skilled in the art.

In operation, wafers 140 such as a disc-like wafers formed from silicon, sapphire, silicon carbide, or other crystalline substrates, are disposed the pockets 92 of each wafer carrier. As best seen in FIGS. 1 and 2, the wafer is disposed with a top surface facing upwardly, so that the top surface is exposed at the top or first surface 88 of the wafer carrier. The opposite, bottom surface of the wafer rests on supports 98 at the periphery of the wafer. The supports engage only a small portion of the bottom surface. The remainder of the bottom surface confronts the floor surface 94 of the pocket, but is elevated above the floor surface so that there is a gap between the bottom surface 128 of the wafer and the floor surface 94 of the pocket.

In a typical cycle of the chemical vapor deposition process, a wafer carrier 80 with wafers loaded thereon is loaded from antechamber 76 into chamber 10 and placed in the operative position shown in FIG. 1. In this condition, the top surfaces of the wafers face upwardly, towards the gas inlet structure 12. Heater 70 is actuated, and the rotary drive 26 operates to turn spindle 20 and hence wafer carrier 80 around axis 22. Typically, the spindle is rotated at a rotational speed from about 50-1500 revolutions per minute.

Heater 70 transfers heat to the bottom surface 90 of the wafer carrier, principally by radiant heat transfer. The heat applied to the bottom surface of the wafer carrier flows upwardly through the body 82 of the wafer carrier to the top surface 88 of the wafer carrier. Heat passing upwardly through the body also passes upwardly through the gaps to the bottom surface of each wafer, and upwardly through the wafer to the top surface of the wafer. Heat is radiated from the top surface 88 of the wafer carrier and from the top surfaces 126 of the wafer to the colder elements of the process chamber as, for example, to the walls of the process chamber and to the gas inlet element 12. Heat is also transferred from the top surface 88 of the wafer carrier and the top surfaces 126 of the wafers to the process gas passing over these surfaces.

Process gas supply 14 is actuated to supply gases through the gas inlet element 12. The gases pass downwardly toward the wafer carrier, over the top surface 88 of the wafer carrier and the top surfaces of the wafers, and downwardly around the periphery of the wafer carrier to the outlet and to exhaust system 18. The process may include an annealing step, in which the process gas supply unit supplies only non-reactive gasses while the wafers and carrier are maintained at an elevated temperature, followed by one or more active deposition periods in which the process gas supply unit supplies reactive gases. The reactive gasses form the desired deposits on the wafers, and also form deposits on the carrier. After completion of the cycle, the carrier is removed from the reaction chamber and replaced with another carrier having additional wafers thereon. After removal from the reaction chamber, the carrier is cleaned to remove deposits from the first surface, and the same carrier is used again in another cycle. For example, the carrier can be baked in an inert atmosphere or vacuum at a temperature higher than that used in the deposition cycle to evaporate deposited material. It is important to remove the deposited material so as to avoid contamination of the wafers used in a subsequent cycle. This process is repeated so that each carrier is used in a sequence of deposition cycles, typically with cleaning after each cycle or after a predetermined number of cycles.

Tool 120 and computer 133 can be actuated to acquire an image of the first surface of the carrier, including wafers loaded thereon, during the annealing step of each cycle, before introduction of reactive gasses. The image in each cycle can be compared to a standard or to an image of the carrier acquired during an earlier cycle. Merely by way of example, this comparison can be done by visual inspection of the displayed images. Because the material deposited on the carrier during a deposition cycle typically has, for example, different emissivity that the emissivity of the carrier surface, an image which represents emissivity will show areas that bear contaminants. If the carriers are not baked (without wafers) in an oven (usually under vacuum) for a period of time, or if residual GaN or other deposited material is left on the carrier, it can be desorbed off of the carrier during the subsequent initial thermal anneal portion of the next growth run. Since the wafers run at a cooler temperature than the wafer carrier, the desorbed GaN deposits preferentially upon the wafers and affects the nucleation process (surface coverage of the nucleation), and thus affects the crystalline properties of the next growth run. Also, where the carrier has a coating such as a silicon carbide coating, cracks in the coating will expose underlying material having a different emissivity, and thus will be readily apparent in the image. Even without a coating, surface irregularities such as nicks or cracks will act as black bodies, and thus emit more intensely than the surrounding surface. These scans allow an operator to determine the end of life for a particular carrier based upon the thermal non-uniformity (due to old age, pocket chips, cracks or voids in the coating, etc.). Historical scans of the carriers can be compared, and as features evolve, it can be determined if a non-uniform carrier will affect future LED runs. Microcracks in the coatings allow, for example, radical hydrogen penetration during the growth process (from pyrolysis of $NH_3$) which desorbs oxygen and carbon from the carrier, which can then be incorporated into subsequently grown LEDs. These contaminants affect LED brightness and electrical properties of the grown films. Cracks act as a blackbody and show up as small, localized brighter regions. When other surface characterization tools are used, similar data, for example, reflectance, can also be acquired and compared with a standard or reference wafer carrier.

If a wafer is out of position, the wafer surface will have a different temperature distribution than the other wafer surfaces, and this can be readily detected by examination of the image.

In other cases, evaluation of the images can identify other non-uniform or incorrect conditions. For example, the image acquisition step can be performed during the active deposition stage of each cycle, as well as during the annealing stage. In the active deposition step, each wafer may bow (or show curvature) as indicated at 140' in FIG. 4. If the wafer bows (or shows curvature) enough to contact the floor surface 94 of the pocket, the wafer will have a hot spot at the point of contact. This can be readily detected by examination of the image by using, for example, a pyrometer or a combination pyrometer/reflectometer or a combined deflectometer/reflectometer/temperature tool. The bowing/curvature of the wafer(s) can be verified by measuring the within-wafer thermal profiles (center to edge) and setting an upper and lower limit for passing criteria. The verification of bowing/curvature of unprocessed wafers can also be evaluated in the same manner.

Other non-uniformities during the process can be similarly detected. Also, changes in the properties of individual wafer carries can be detected using the images and, particularly, by comparing an image to a previously-acquired image of the same carrier. For example, if scans are conducted within the MOCVD reactor during the initial anneal portion of the growth run (where wafers are loaded on a carrier), then it is possible to tell if a wafer is misloaded due to the thermal profile of it compared to its peers (within a given ring). It is possible for small particles or other features to get lodged under the wafers when they are loaded, creating non-ideal thermal contact with the wafer carrier. In this case, the wafer will run with either a different absolute temperature, or a gradient in temperature (if it is tilted), thereby affecting the within-wafer and wafer-to-wafer wavelength yield during the growth.

In-situ scans, using the surface characterization tools disclosed herein, of the wafer carrier can also be performed to make sure that the wafer carrier is uniform during semiconductor growth. The scans would allow an independent measurement to make sure that the temperature is uniform across the wafer carrier as well as detect any temperature variations within the wafer carrier.

The operator, or an automated system, can take appropriate action to control or modify the process based at least in part on examination of the images. For example, the operator can identify wafer carriers which have deteriorated or which have not been properly cleaned and can remove the carriers from the process.

Figure 5:
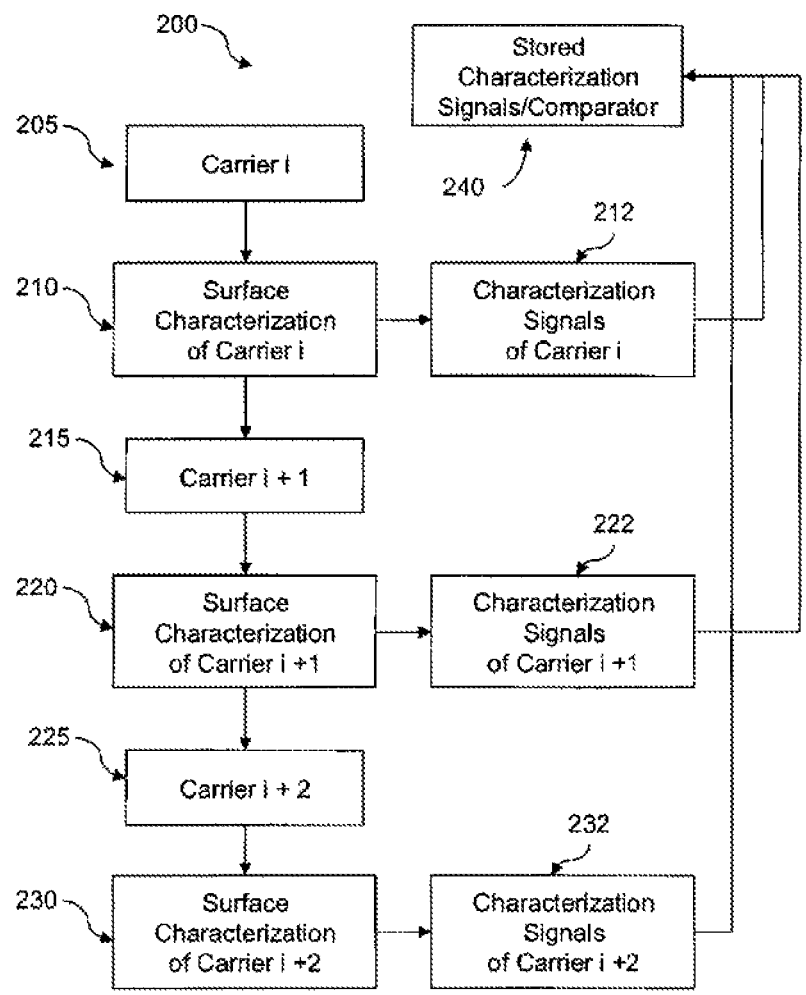
FIG. 5 is a schematic drawing relating to a method of evaluating a carrier.

FIG. 5 shows an outline of a method for evaluating wafer carriers. Schematic 200 shows a sequence of a plurality of carriers i, i+1, i+2, etc can be evaluated, or characterized, and the characterization signals stored. The stored signals can then be used to compare wafer carrier top surfaces to see, for example if there are variations in a lot or batch of wafer carriers as well as used to determine whether the wafer carrier, after being subjected to a number of CVD processes and cleanings, is still suitable for use; that is, whether there are any defects on the top surface of the wafer carrier that can affect yield and/or whether the wafer carrier surface has been properly cleaned to remove deposited materials. Additionally, each wafer carrier can be scanned and its characterization signals stored so that the same wafer can be compared against itself after one or more CVD processes to see if the carrier has been properly cleaned and/or damaged during the CVD process and/or cleaning process. In this manner, non-suitable wafer carriers can be removed before loading with wafers, increasing the yield of LEDs per wafer.

At step 205, carrier i, which can be obtained from a lot or batch of wafer carriers, is placed in a suitable apparatus that allows for rotation of the carrier as well as heating the carrier to an evaluation temperature, usually within a range of from about 400° C. to about 1500° C. One or more of the surface characterization tools mentioned herein are mounted onto a track (similar to track 130 discussed above). The wafer carrier is then heated to a predetermined temperature and the surface characterization of the top surface of carrier i takes place at step 210 and the characterization signals are acquired at step 212 and stored at step 240. The storage of the signals and comparator in step 240 can be done in a variety of ways, from recording the signals in a notebook and making a side by side comparison of the signals to storing the data in a computer which has a set of instructions to make data comparisons.

After the surface characterization of carrier i has taken place, carrier i is removed from the apparatus and stored for later use. Then, carrier i+1 is then loaded at step 215 and undergoes the same process as carrier i at steps 220 and 222 with the characterization signals being stored at step 240. As before, after the surface characterization of carrier i+1 has taken place, carrier i+1 is removed from the apparatus and stored for later use. Then, carrier i+2 is then loaded at step 225 and undergoes the same process as carrier i+1 at steps 230 and 232 with the characterization signals being stored at step 240.

At step 240, after a set of carriers have been characterized, the comparator can then be run to determine if the carriers that have been evaluated meet, for example, specifications or if any of the carriers have been damaged during shipment (for example, chips or cracks in the SiC coating on the top surface of the carrier). Additionally, the comparison of the signals can determine if there is a wide or narrow range of difference between the signals of the individual carriers as well as determining the surface uniformity of each carrier top surface. If there is a wide range of difference in the signals of the individual carriers, that could be an indication of manufacturing issues which could lead to reduced yield of LEDs should the carriers be used in production. If a narrow range is found, this could be an indication that carriers were manufactured to appropriate specifications and are usable for LED production. Temperature variation of a carrier top surface, which can be, for example, in terms of a temperature gradient across the entire carrier top surface or as a standard deviation across the carrier top surface can be one way to determine surface uniformity. Based on the types of LEDs to be manufactured, for example GaN based or AsP based, the temperature gradient or temperature standard deviation may be very small.

For the situation where a narrow range is found, a random carrier can be selected by, for example, an operator or a computer. The randomly selected carrier can then act as a reference carrier against which the carriers in a particular lot or batch of carriers, which included the randomly selected carrier, can be compared. The comparison can be done in a manner as described in FIG. 5 above or in FIG. 6 below. The comparison can be done as the carriers from a particular lot or batch of carriers are evaluated against the carriers in a particular batch or lot, against carriers in different lots or batches from the same manufacturer, or as the carriers in a particular batch or lot proceed through various CVD process steps and are evaluated in the various steps as discussed within this disclosure. For the situation where a wide range of difference in the signals of the carriers, the wide range being dependent upon the company or client standards and requirements, this does not necessarily mean that the particular lot or batch has to be considered as not meeting specifications. In some instances, a more rigorous statistical analysis can be done on the signal data to determine if there is a random carrier which fits the specific company or client standards and requirements. It is likely that after a rigorous statistical analysis, a random carrier can be selected and this carrier can then be used as described within this disclosure.

Figure 6:
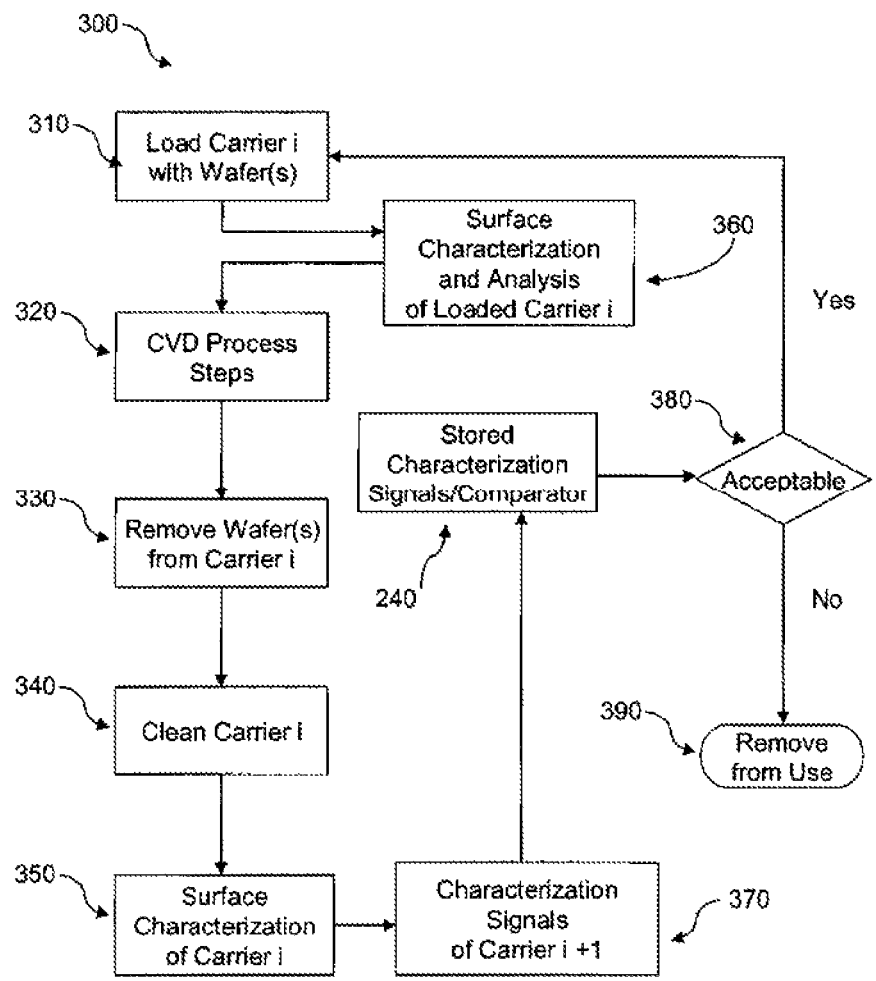
FIG. 6 is a schematic drawing relating to another method of evaluating a carrier.

FIG. 6 shows a schematic 300 of another method to inspect carriers. In this schematic, at step 310, a wafer carrier i, loaded with wafers is placed into a chemical vapor deposition chamber. Prior to the deposition stage of the process, for example, during the annealing stage, the carrier and wafers are heated to a predetermined temperature and surface characterization and analysis of the loaded carrier i takes place at step 360. During this step, it can be determined whether the wafers are properly loaded onto carrier i and/or whether there are any defects on carrier i that were missed during a previous inspection.

If carrier i and wafers in step 360 are found to be acceptable, then loaded carrier i can then proceed with the full CVD process in step 320. If carrier i and/or the wafers in step 360 are found not to be acceptable, then the operator can decide, based on protocols set up by a company or client, to, for example, take the carrier off-line and reload the wafer(s) that may not be properly loaded on the carrier, scrap the entire carrier and/or wafers, or any other step that might have an impact on the yield of LEDs from the particular carrier/wafer arrangement.

With carrier i and wafers having undergone the CVD process in step 320, carrier i and wafers are moved to a chamber or apparatus where the wafers that have undergone a CVD process are removed for further processing. Carrier i is then moved in step 340 to a cleaning step, which can, for example, involve placing the carrier in an oven under an inert atmosphere or vacuum at a temperature higher than that used in the deposition cycle to evaporate deposited material, using a halide-based vapor etch, acid-based etching, physical cleaning such as sand blasting or $CO_2$ impingement, and the like.

Thereafter, once carrier i is cleaned, it can either be placed in storage area for future use or put back in a queue for wafer loading and subsequent CVD processing. Prior to loading, carrier i can then be evaluated in a manner similar to that described above in schematic 200 in FIG. 5 at step 350 of FIG. 6. The characterization signals are acquired at step 370 and stored at step 240, which can be the same or different comparator used in Schematic 200. In most instances, it will be more useful to have it be the same. In this manner, carrier i's original characterization signals prior to any CVD processing can then be compared against the characterization signals of carrier i that were obtained after being cleaned. Based on criteria developed by the user, a determination can be made at step 380 to determine whether cleaned carrier i is still suitable for use, based on a comparison between the characterization signals of the cleaned carrier and the characterization signals from the carrier when it was initially examined. If carrier i is found to be acceptable, it is then returned to step 310 to be loaded with wafers and then the additional steps in Schematic 300 until such time that the comparison at step 380 shows that the carrier i is no longer acceptable. In that instance, the carrier is removed from use at step 390.

Figure 7:
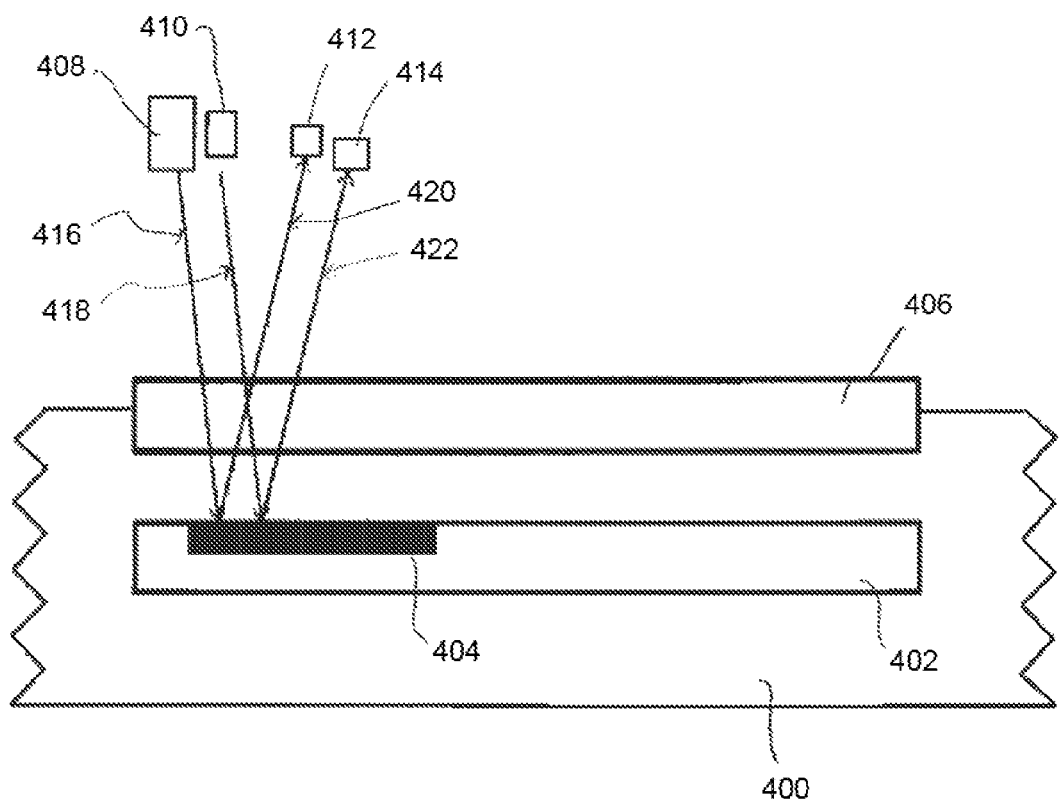
FIG. 7 is a fragmentary sectional view relating to evaluation of a wafer.

FIG. 7 shows one example of a surface acoustic wave generator system as described hereinabove. Cutaway portion 400 of a MOCVD reactor shows wafer carrier 402, holding wafer 404, and view port 406. A laser 408 generates a surface acoustic wave by sending an incident beam 416, which then bounces off the surface of wafer 404 with the reflected beam 420 being detected by detector 412. At the same time, another laser 410 sends an incident beam 418 to detect the surface acoustic wave generated by incident beam 416 from laser 408. Incident beam 418 bounces off the surface of wafer 404 with a reflected beam 422 which is detected by detector 414. As described above, an analysis of the reflected beams can be used to measure and monitor the thickness of films grown on wafer 404 as well as the optical reflectivity of the film/wafer structure. The film/wafer structure and resulting information measured through the surface acoustic wave generator system can be used to adjust recipe and process conditions on a run to run basis, allowing for greater control of the reactor and improved quality of LED devices from run to run. The placement of lasers 408 and 410 and detectors 412 and 414 in relation to view port 406 and wafer carrier 402 can vary, depending upon the needs of the operator. In some instances, lasers 408 and 410 can be located within the reactor mezzanine and the detectors 412 and 414 can be mounted on a translation stage that moves along view port 406. This kind of arrangement allows for surface acoustic wave generator to measure and monitor film thickness and wafer temperature as well as generating film reflectivity topology maps of the wafer surface when wafer carrier 402 rotates within the MOCVD reactor.

From the methods disclosed herein, quality control of wafer carriers for good/bad thermal uniformity can be maintained. The emissivity (blackness) of SiC coating on the wafer carrier is a function of the stoichiometry and thickness of the SiC coating. "Greyness" measurements of the wafer carriers at room temperature are hard to analyze, but if heated above about 400° C., thermal scans of the wafer carrier can show subtle differences in the coating. Emissivity of the carriers can also change (increase) as they are used, possibly due to changing microroughness of the SiC coating surface. The emissivity can be monitored by mapping the wafer carriers as a function of heating power over time.

Numerous various and combinations of the features discussed above can be employed. The wafer carrier may include more or fewer wafer-carrying regions than shown and discussed above. The configurations of the wafer-carrying regions can be varied. Also, tool 120 can be replaced by a thermal imaging camera. As referred to herein, a camera is tool which simultaneously acquires data representing characterization signal emanating from a plurality of points or small regions. In a further variant, the images of the carriers can be obtained while the carriers are disposed outside of the reaction chamber. For example, the carriers can be imaged in the antechamber 76 or in an entirely separate unit.

In a further variant, the viewpoint of the tool can be scanned without moving the tool. For example, where the tool is arranged to receive characterization signal from the carrier by way of a mirror, the mirror can be moved so as to move the viewpoint.

Another embodiment of the present invention is to use the method and/or apparatus disclosed herein to match reaction chambers and/or wafer carriers by obtaining, for example, thermal maps or 'thermal signatures' from a control wafer carrier and/or chamber and then optimizing the chamber and/or wafer carrier conditions of other CVD or MOCVD reaction systems (including wafer carriers). Other types of maps can be generated using typical metrology tools used in the semiconductor industry and which are well known to those skilled in the art. The system comprises a surface characterization tool adapted to measure a surface characteristic over a plurality of positions relative to a rotatable carrier having a top surface adapted to hold at least one semiconductor wafer, where the surface characterization tool is adapted to produce characterization signals, which contain information about the top surface of the carrier and/or wafer, over the plurality of positions, and a first computer having a memory for storing a set of computer instructions, where the computer is in communication with the surface characterization tool for determining values for position-dependent parameters characterizing the top surface of the carrier based on the characterization signals obtained during each process step of a chemical vapor deposition run. In addition there is a chemical vapor deposition chamber in which a carrier rotatable about an axis of rotation and having a top surface adapted to hold at least one semiconductor wafer with a major surface of the wafer extending generally transverse to the axis of rotation is placed. A second computer has a memory for storing a set of computer instructions, including instructions for adjusting process conditions for each step of a chemical vapor deposition run, is also provided and is communication with first computer. The first computer can communicate the position-dependent parameters from the surface characterization tool during each step of a chemical vapor deposition run to the second computer, which can then adjust the process conditions of each step of a chemical vapor deposition run to improve or increase yield in the chamber. In the chamber can be placed a heater which is proximately placed to the carrier. The heater has one or more heating elements. Additionally, one or more gas sources, to supply gases including a Group III metal source and a Group V compound into the chamber can be provided. The second computer can be in communication with the heater and/or gas sources, which can then be adjusted based on communications between the first computer and the second computer.

For example, during each step of the chemical vapor deposition run which can be performed in a control reactor system, which can include a control wafer carrier, a thermal characterization of the wafer carrier can be done and recorded along with the temperature of the reaction chamber and/or the wafer carrier heaters. Wafer characterization can also be performed and quality and yield can be correlated against the thermal characterization of the wafer carrier and the temperature of the reaction chamber and/or the wafer carrier heaters. Deposition conditions can be modified and optimized to minimize or eliminate defects in the growth layers during the various deposition cycles and the surface characterization signals from the control reactor and/or wafer carriers can be transmitted to other reactors via a controller or computer which have instructions on how to change the operating conditions of the reactor, from gas flow to temperature zones of the wafer carrier (or reactor) to impart the optimized reaction conditions the control reactor and/or wafer carrier to another reactor.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of characterizing a surface comprising:
   rotating a carrier about an axis of rotation, the carrier having a top surface adapted to hold at least one semiconductor wafer with a major surface of the wafer extending generally transverse to the axis of rotation;
   moving a surface characterization tool over a plurality of positions relative to the top surface of the carrier, whereby a measurement location over the top surface of the carrier is changed, while said top surface of the carrier is heated to a predetermined temperature;
   producing characterization signals over the plurality of positions with the surface characterization tool, the characterization signals containing information about the heated top surface of the carrier;
   determining values for position-dependent parameters characterizing the top surface of the carrier based on the characterization signals;
   comparing the position-dependent parameters characterizing the top surface of the carrier to a reference carrier top surface, wherein the reference carrier top surface is determined by performing the rotating, moving, producing, and determining steps on a randomly selected carrier; and
   reviewing the position-dependent parameters characterizing the top surface of the carrier based on the characterization signals against predetermined acceptable parameters.

2. The method of claim 1 further comprising displaying the position-dependent values in a perceptually visible form.

3. The method of claim 1 wherein a plurality of carriers are characterized, the carrier is a first carrier and the position-dependent parameters characterizing the top surface of the carrier is a first carrier top surface position-dependent parameters, further comprising
   producing characterization signals over the plurality of positions with the surface characterization tool, the characterization signals containing information about the top surface of a second carrier while being heated; and
   comparing the first carrier top surface position-dependent parameters to the second carrier top surface position-dependent parameters.

4. The method of claim 3 wherein the comparison is displayed in a perceptually visible form.

5. The method of claim 3 further comprising producing characterization signals over the plurality of positions with the surface characterization tool, the characterization signals containing information about the top surface of a third carrier while being heated; and producing characterization signals over the plurality of positions with the surface characterization tool, the characterization signals containing information about the top surface of a fourth carrier while being heated.

6. The method of claim 1 wherein a plurality of carriers are characterized, the reference carrier top surface is on a randomly selected first carrier, further storing the characterization signals from the reference carrier top surface in a database.

7. The method of claim 6 wherein the randomly selected first carrier is obtained from a single production lot or batch of carriers.

8. The method of claim 1 further comprising performing the steps of claim 1 on a second carrier; and comparing the position-dependent parameters characterizing the top surface of the second carrier to the position-dependent parameters characterizing the top surface of the reference carrier.

9. The method of claim 8 wherein the second carrier has undergone a chemical vapor deposition run and a cleaning step to remove residual deposits from the chemical vapor deposition run.

10. The method of claim 1 wherein the reference carrier is a carrier that has not undergone a chemical vapor deposition run.

11. The method of claim 1 wherein the predetermined temperature ranges from about 200° C. to about 1500° C.

12. The method of claim 1 further comprising storing the characterization signals from the top surface of the carrier in a database.

13. The method of claim 12 further comprising causing the carrier, onto which at least one semiconductor wafer is being held, to undergo a chemical vapor deposition run, wafer removal, and subsequent cleaning to remove residual deposits from the chemical vapor deposition run on the top surface of the carrier; and repeating the steps of claim 1 on the cleaned top surface of the carrier.

14. The method of claim 13 further comprising comparing the position-dependent parameters characterizing the top surface of the cleaned carrier to the position-dependent parameters characterizing the top surface of the carrier which did not undergo the chemical vapor deposition run to determine if the top surface of the cleaned carrier is acceptable.

15. The method of claim 14 wherein the comparison is displayed in a visually perceptible form.

16. The method of claim 14 which is repeated on the cleaned carrier until the top surface of the carrier is no longer acceptable.

17. The method of claim 1 wherein the carrier is holding at least one semiconductor wafer.

18. The method of claim 17 wherein when the carrier is holding at least one semiconductor wafer, the surface characterization tools measure a surface property selected from temperature of the semiconductor wafer, bowing of the semiconductor wafer, warping of the semiconductor wafer, and tilting of the semiconductor wafer.

19. The method of claim 18 wherein the surface characterization tool is selected from a pyrometer, reflectometer, a combined pyrometer/reflectometer, a combined deflectometer/reflectometer/temperature tool, ellipsometer, photoluminescence spectrometer, camera, electroluminescence spectrometer, surface acoustic wave generator, or any combination thereof.

20. The method of claim 19 wherein the pyrometer is a pyrometer which operates at a wavelength of from about 400 nm to about 8 µm.

21. The method of claim 1 wherein the surface characterization tool is selected from a pyrometer, reflectometer, a combined pyrometer/reflectometer, a combined deflectometer/reflectometer/temperature tool, ellipsometer, photoluminescence spectrometer, camera, electroluminescence spectrometer, surface acoustic wave generator, or any combination thereof.

22. The method of claim 21 wherein the pyrometer is a pyrometer which operates at a wavelength of from about 400 nm to about 8 µm.

23. The method of claim 21 wherein the surface characterization tools measure a surface property selected from temperature, reflectance, photoluminescence, electroluminescence, emissivity, and absence or presence of residual deposits from a chemical vapor deposition run.

24. The method of claim 21 further comprising:
linking the surface characterization tool to one or more feedback loops, the one or more feedback loops providing signals to adjust the temperature of the carrier.

25. A method of characterizing a surface comprising:
rotating a carrier about an axis of rotation, the carrier having a top surface adapted to hold at least one semiconductor wafer with a major surface of the wafer extending generally transverse to the axis of rotation;
moving a surface characterization tool over a plurality of positions relative to the top surface of the carrier, whereby a measurement location over the top surface of the carrier is changed;
producing characterization signals over the plurality of positions with the surface characterization tool, the characterization signals containing information about the top surface of the carrier;
determining values for position-dependent parameters characterizing the top surface of the carrier based on the characterization signals;
comparing the position-dependent parameters characterizing the top surface of the carrier to a reference carrier top surface, wherein the reference carrier top surface is determined by performing the rotating, moving, producing, and determining steps on a randomly selected carrier; and
reviewing the position-dependent parameters characterizing the top surface of the carrier based on the characterization signals against predetermined acceptable parameters.

26. The method of claim 25 wherein the carrier and/or wafer is heated to a predetermined temperature, the heating being accomplished by a heater having one or more heating elements.

27. The method of claim 26 wherein the surface characterization tool is selected from a pyrometer, reflectometer, a combined pyrometer/reflectometer, a combined deflectometer/reflectometer/temperature tool, ellipsometer, photoluminescence spectrometer, camera, electroluminescence spectrometer, surface acoustic wave generator, or any combination thereof.

28. The method of claim 27 wherein the pyrometer is a pyrometer which operates at a wavelength of from about 400 nm to about 8 µm.

29. The method of claim 27 wherein the surface characterization tools measure a surface property selected from temperature, reflectance, photoluminescence, electroluminescence, emissivity, and absence or presence of residual deposits from a chemical vapor deposition run.

30. The method of claim 27 wherein when the carrier is holding at least one semiconductor wafer, the surface characterization tools measure a surface property selected from temperature of the wafer, bowing of the semiconductor wafer, warping of the semiconductor wafer, and tilting of the semiconductor wafer.

31. The method of claim 30 wherein the surface characterization tool is selected from a pyrometer, reflectometer, a combined pyrometer/reflectometer, a combined deflectometer/reflectometer/temperature tool, ellipsometer, photoluminescence spectrometer, camera, electroluminescence spectrometer, surface acoustic wave generator, or any combination thereof.

32. The method of claim 31 wherein the pyrometer is a pyrometer which operates at a wavelength of from about 400 nm to about 8 µm.

33. The method of claim 26 further comprising:
linking the surface characterization tool to one or more feedback loops, the one or more feedback loops providing signals to adjust the heater.

* * * * *